United States Patent [19]

Tadros

[11] Patent Number: 5,139,773
[45] Date of Patent: Aug. 18, 1992

[54] PESTICIDAL FORMULATIONS

[75] Inventor: Tharwat F. Tadros, Wokingham, England

[73] Assignee: Imperial Chemical Industries PLC, London, England

[21] Appl. No.: 186,437

[22] Filed: Apr. 26, 1988

[30] Foreign Application Priority Data

Apr. 29, 1987 [GB] United Kingdom ............... 8710105

[51] Int. Cl.⁵ .................. A01N 25/04; A01N 25/22; A01N 43/00
[52] U.S. Cl. .................................. 514/315; 514/383; 514/400; 514/975
[58] Field of Search .................. 424/78, 81, 78.1; 514/383, 400, 975; 523/122

[56] References Cited

U.S. PATENT DOCUMENTS

| | | | |
|---|---|---|---|
| 4,243,403 | 1/1981 | Lewis et al. | 523/122 |
| 4,566,906 | 1/1986 | McGinnis et al. | 523/122 |
| 4,596,724 | 6/1986 | Lane et al. | 523/122 |
| 4,654,380 | 3/1987 | Makepeace | 523/122 |
| 4,734,432 | 3/1988 | Szegö514 | 469/ |
| 4,745,114 | 5/1988 | Elliott et al. | 514/320 |
| 4,752,629 | 6/1988 | Proudlock et al. | 523/122 |

FOREIGN PATENT DOCUMENTS

| | | | |
|---|---|---|---|
| 549277 | 4/1957 | Canada | 523/122 |
| 0040007 | 11/1981 | European Pat. Off. | 514/383 |
| 992551 | 1/1983 | U.S.S.R. | 523/122 |
| 583204 | 9/1959 | United Kingdom | 523/122 |
| 2026341 | 7/1979 | United Kingdom . | |

Primary Examiner—Merrell C. Cashion, Jr.
Assistant Examiner—Choon Koh
Attorney, Agent, or Firm—Cushman, Darby & Cushman

[57] ABSTRACT

Mixtures of different pesticides, in emulsion and suspension form respectively, are stabilized by incorporation in the mixture of the emulsion and suspension a dispersant capable of being strongly adsorbed onto the particles of the pesticide in suspension form, such a dispersant being a block of graft copolymer as described in UK Patent Specification Number 2026341-A and/or 1196248.

14 Claims, No Drawings

PESTICIDAL FORMULATIONS

This invention relates to pesticidal, especially fungicidal and herbicidal, formulations. More particularly the invention relates to formulations containing more than one active ingredient, that is to say more than one pesticide.

In recent years it has proved useful, for a number of reasons, to formulate fungicides and herbicides as mixtures containing at least two different active ingredients. In this way, for example, a wider spectrum of fungal diseases and weeds can be combatted, and, at the same time it is often possible to overcome problems caused by the development of resistance by fungi to known fungicides. Such resistance may be demonstrated to one, or even both, of the active fungicidal substances formulated together in the same mixture. Another benefit that can accrue from mixtures of two or more fungicidal substances is the effect of synergism, that is to say there is some interaction between the fungicidal substances in the mixture such that an enhancement of activity, be it in intensity or spectrum, or both, for example, occurs. In the event more, or the same, diseases are combatted more effectively than might be expected or predicted from a simple summation of the individual effects of the component pesticides in the mixture.

There have been problems, recognised for some time, however, in effectively formulating two or more active ingredients into a satisfactory mixture, more especially when the physical and/or chemical properties of the different active substances are such as to present compatibility problems. Indeed some fungicidal substances are difficult to formulate by themselves and may only be effectively formulated in one particular way, for example as an emulsion or a suspension. Particularly difficult problems can arise in the latter instance, for example in the preparation of a stable suspension/emulsion mixture of one pesticide formulated as a suspension, for example because of solubility difficulties, and another formulated as an emulsion, for example as an oil-in-water emulsion. Thus there can be unfavourable interaction between the droplets and particles on the one hand, and between the emulsifiers and dispersants on the other leading to a breakdown of the formulation. Thus flocculation can occur as a result of interaction between the emulsifiers of the oil (in an oil-in-water emulsion) and the dispersants used to disperse the particles in a suspension. It is believed that the surfactants used as emulsifiers in the emulsions may displace the dispersing agents adsorbed to the particles in the suspension. Moreover, if either the dispersants and/or emulsifiers are not strongly adsorbed, flocculation may result from interaction of resultant "bare" patches on the droplets or the particles (by Van der Waals attraction). We have now found that by using certain dispersing agents for the formulated mixture such flocculation can be substantially reduced or even avoided. It has further been discovered that the additional problem caused by the tendency for transfer (e.g. migration) of the particles of the active ingredient of the suspension to the oil phase of the emulsion of the other active ingredient, and there to crystallize, is reduced by the use of certain dispersing agents, with or without the presence of a crystal growth inhibitor.

According to the present invention, therefore, there is provided a pesticidal formulation comprising a mixture of an active ingredient formulated as an emulsion and one or more active ingredients each formulated as a suspension wherein there is present a dispersing agent which is, or comprises, a block or graft copolymer the molecule of which comprises at least one component (A), of molecular weight at least 250, which is solvatable by the aqueous medium and at least one other component (B), of molecular weight at least 500 and having a minimum degree of hydrophobicity as hereinafter defined, the total weight ratio of components A to individual components B in the copolymer molecule being from 10:1 to 1:2.

By "solvated" or "solvatable" we mean herein that the molecular component A of the block or graft copolymer would, if it were unattached to the remainder of the copolymer molecule, be actually soluble in the aqueous medium wholly as individual molecules. Such block or graft copolymers are described in UK Patent Specification No. 2026341A.

By "minimum degree of hydrophobicity" we mean that the component B of the block or graft copolymer would, if it were unattached to the remainder of the copolymer molecule, be sufficiently hydrophobic to be insoluble both in water and in methanol. The word "insoluble" is to be understood here as having its ordinary, practical meaning.

As an alternative, the dispersing agent can be one as described in UK Patent Specification No. 1196248. Thus it can be an amphipathic polymeric stabiliser capable of associating with and entropically stabilising a non-ionic dispersion of particulate solids in an aqueous liquid and comprising a polymeric backbone provided by a random copolymer, of alpha,beta-ethylenically unsaturated monomers with a molecular weight of at least 10,000, optionally containing ionizable groups, which is per se insoluble in the aqueous liquid, the polymeric backbone carrying at least two pendant chain-like non-ionic components of molecular weight at least 350 solvated by the aqueous liquid and distributed along the said backbone at intervals of less than 30 covalent links, the weight proportion of components solvated by the aqueous liquid being from 20 to 80 of the stabiliser molecule.

The subject-matter of UK Patent Specification Nos. 2026341-A and 1196248 is therefore herein incorporated by reference. A particularly preferred dispersing agent is Polymeric Surfactant H190/396 which is described in detail hereinafter and which is of the class of dispersing agents known as "comb" Surfactants. The formulations of the invention can also comprise, with advantage, a crystal growth inhibiting substance, e.g. a dye such as Fast Green FCF.

The following procedure may be used to prepare the formulations of this invention.

The pesticide or pesticides formulated as a suspension are solids, and are milled, e.g. by bead milling, with water and a surfactant such as "MORWET" D425 or "POLYFON" H, or, as an alternative, with the Polymeric Surfactant H190/396, to form a millbase or millbases. This (or these) can be added to the emulsion of the other pesticide as a final stage, preferably by stirring it (or them) into the emulsion of the other pesticide component using a mixer.

The other pesticide ingredient is formulated as an oil-in-water emulsion. Thus the active chemical ingredient can, if necessary, be dissolved in an organic solvent, e.g. xylene, toluene or the like, if necessary as a supersaturated solution to achieve the desired concentration, and using surface agents, such as, for example sorbitan mono-oleate and polyoxyethylene sorbitan mono-palmitate (e.g. "SPAN" 80 and "TWEEN" 40).

Thus the procedure to form the emulsion of the other pesticide component can be, for example, to dissolve the pesticide in a solvent, such as xylene, or "SOLVESSO" 150, if necessary warming to, say, about 50° C. to achieve dissolution. The surfactant or surfactants, e.g. "SPAN" 80, "TWEEN" 40, and "SYNPERONIC" NPE 1800, are likewise dissolved into the solvent either simultaneously with the pesticide or immediately afterwards. Emulsification is then effected using a mixer, e.g. a high-shear stirrer, and this oil is added to an aqueous phase comprising water, urea if desired, and a high molecular weight polysaccharide, such as a Xanthan gum, e.g. "KELZAN" M. The "KELZAN" M is preferably pre-swollen by adding water to it to form a gel in which a bactericide, e.g. "PROXEL" AB, may be incorporated. Other additives to the aqueous phase may be (a) polyvinyl alcohol containing about 10% of polyvinyl acetate, e.g. "GOHSENOL" GL05, (b) a bentonite clay, e.g. "BENTOPHARM" and (c) a crystal growth inhibitor, e.g. Fast Green FCF; and the dispersing agent, e.g. Polymeric Surfactant H190/396, is also added to the aqueous phase (if not incorporated in the millbase). However, the polymeric surfactant and the high molecular weight linear polysaccharide can, if desired, be added to the emulsion along with the millbase (or millbases) in a final stage, mixing being continued for several minutes thereafter.

The invention further provides, therefore, a process for preparing a mixture of pesticides which comprises milling one or more of the pesticides with water and a surfactant to form one or more millbases, dissolving a further pesticide, in a solvent if necessary, dissolving a surfactant in this oil phase, if necessary with warming, and then, using a high shear mixer for several minutes, emulsifying the solution together with water, urea if desired, and also, if desired, a high molecular weight linear polysaccharide formed as a gel by pre-swelling with water and optionally containing a bactericide, and a dispersing agent as hereinbefore defined, thereafter stirring the millbase, or millbases, into the emulsion so formed as a final stage. The surfactant used in the solution of the further pesticide is either (a) a condensate of nonyl phenyl with alkylene oxides, e.g. "SYNPERONIC" NPE 1800, or (b) sorbitan mono-oleate, e.g. "SPAN" 80, together with a condensate of sorbitan monopalmitate with ethylene oxide, e.g. "TWEEN" 40.

In an alternative procedure the dispersing agent, e.g. Polymeric Surfactant H 190/396, and the high molecular weight linear polysaccharide, e.g. "KELZAN" M, are added to the emulsion along with the millbase or millbases in the final stage.

The invention is particularly useful in the preparation, and provision, of mixtures comprising, as active ingredients the following:

| Suspension Pesticide | Emulsion Pesticide | Additional Suspension Pesticide |
|---|---|---|
| Flutriafol | Propiconazole | — |
| Flutriafol | Imazalil | — |
| Diclobutrazol | Imazalil | — |
| Carbendazim | Prochloraz | — |
| Propyzamide | Fluazifop-P-butyl | — |
| Diclobutrazol | Prochloraz | — |
| Chlorothalonil | Tridemorph | Hexaconazole |

-continued

| Suspension Pesticide | Emulsion Pesticide | Additional Suspension Pesticide |
|---|---|---|
| Chlorothalonil | Fenpropidin | Hexaconazole |

All the foregoing pesticides are referred to by their common names and are fully described in The Pesticide Manual (Eighth Edition) published by The British Crop Protection Council and printed by The Lavenham Press Ltd, Lavenham, Suffolk, England.

| Pesticide Common Name (Page No. of The Pesticide Manual in brackets) | Chemical Name (IUPAC) |
|---|---|
| Propiconazole (714) | (±)-1-[2-(2,4-dichlorophenyl)-4-propyl-1,3-dioxolan-2-yl-methyl]-1H-1,2,4-triazole |
| Flutriafol (423) | (RS)-2,4'-difluoro-α-(1H-1,2,4-triazol-1-ylmethyl)-benzhydryl alcohol |
| Diclobutrazol (271) | (2RS,3RS)-1-(2,4-dichloro-phenyl)-4,4-dimethyl-2-(1H-1,2,4-triazol-1-yl)pentan-3-ol |
| Imazalil (471) | Allyl 1-(2,4-dichlorophenyl)-2-imidazol-1-ylethyl ether |
| Prochloraz (690) | N-Propyl-N-[2-(2,4,6-trichloro-phenoxy)ethyl]imidazole-1-carboxamide |
| Carbendazim (127) | Methyl 1H-benzimidazol-2-ylcarbamate |
| Propyzamide (720) | 3,5-dichloro-N-(1,1-dimethyl-propynyl)benzamide |
| Fluazifop-P-butyl (405) | Butyl (RS)-2-[4-(5-trifluoro-methyl-2-pyridyloxy)phenoxy]-propionate |
| Chlorothalonil (170) | Tetrachloroisophthalonitrile |
| Hexaconazole (460) | (RS)-2-(2,4-dichlorophenyl)-1-(1H-1,2,4-triazol-1-yl)hexan-2-ol |
| Tridemorph (827) | 2,6-dimethyl-4-tridecyl-morpholine |
| Fenpropidin (382) | (RS)-1-[3-(4-tert-butylphenyl)-2-methylpropyl]piperidine |

The invention is illustrated by the following examples. In these Examples the following substances/adjuvants are referred to. Those in capital letters are Trade Marks.

Polymeric Surfactant H190/396 (Belongs to a class of surfactants described as "Comb").

This is a 33% solids solution in 1/1:water/propylene glycol of an acrylic graft copolymer with non-ionic surface active properties. The acrylic graft copolymer contains 36.6% methyl methacrylate, 1.9% methacrylic acid, both grafted with methoxy poly(ethylene glycol) 750 methacrylate (61.5%).

"MORWET" D425

This is the sodium salt of a condensed naphthalene formaldehyde sulphonate (Petrochemicals Company, Inc. Fort Worth, Tex., USA).

"KELZAN" M

This material is supplied by Kelco, a Division of Merck and Company, Inc., and it is a high molecular weight linear polysaccharide called xanthan gum.

"SPAN" 80

This substance is obtainable from ICI Speciality Chemicals Group and it is sorbitan mono-oleate.

"PROXEL" AB

This is obtainable from ICI Speciality Chemicals Group and it is a 33% fluid aqueous dispersion of 1,2-benzisothiazolin-3-one).

"SOLVESSO" 150

This is a mixture of $C_{10}$ alkylbenzenes.

"SYNPERONIC" NPE 1800

This is a condensate of nonyl phenol with propylene oxide and ethylene oxide.

"POLYFON" H

This is a sodium lignosulphonate.

"BENTOPHARM"

This is a bentonite clay.

"GOHSENOL" GL05

This is a polyvinyl alcohol containing approximately 10% of polyvinyl acetate.

"TWEEN" 40

This is a condensate of sorbitan mono-palmitate with 20 moles of ethylene oxide.

EXAMPLE 1

A formulation was developed containing flutriafol, a crystalline solid, and propiconazole, a low melting point, oil-soluble, solid.

|  | g/l (g/l signifies grams per liter |
|---|---|
| Propiconazole | 70 |
| Flutriafol | 180 |
| Xylene | 54 |
| "SPAN" 80 | 60 |
| "TWEEN" 40 | 40 |
| "GOHSENOL" GL05 | 10 |
| Urea | 135 |
| "MORWET" D425 | 5.6 |
| Polymeric Surfactant H190/396 | 20 |
| "PROXEL" AB | 0.1 |
| Water to one liter | |

The flutriafol was bead milled at 500g/l with the "MORWET" D425 (40g/l) to form a millbase. The propiconazole was dissolved in xylene along with the "SPAN" 80 and the "TWEEN" 40 on warming to 50° C. and the solution was then emulsified into a solution of the water, urea, "KELZAN" M (pre-swollen in water and containing "PROXEL" AB as bactericide), "GOHSENOL" GL05 (predissolved in water at 100 g/l) and the Polymeric Surfactant H190/396. The whole was mixed using a high shear stirrer and mixing was continued for seven minutes after the addition of the emulsion phase. The flutriafol millbase was then stirred in to the emulsion as the final stage.

Propiconazole is a yellowish viscous liquid with a boiling point of 180° C. at 13.2 Pascals. It is a systemic fungicide.

It has the chemical structure:

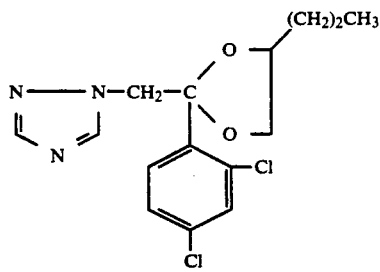

and the following chemical name (IUPAC): (±)-1-[2-(2,4-dichlorophenyl)-4-propyl-1,3-dioxolan-2yl-methyl]-1H-1,2,4-triazole.

Flutriafol is a colourless solid having a melting point of 130° C. It is a systemic fungicide and has the chemical formula:

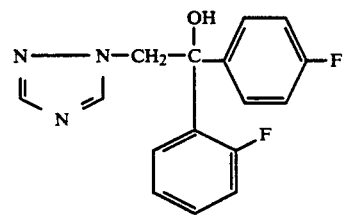

and the following chemical name: (RS)-2,4'-difluoro-alpha (1H-1,2,4-triazol-lylmethyl)-benzhydryl alcohol (IUPAC chemical name).

The foregoing admixture of two fungicides can be used to combat the following fungal diseases of cereal crops.

| Early season diseases: | |
|---|---|
| Eyespot | *Pseudocercosporella herpotrichoides* |
| Netblotch | *Ryrenophora teres* |
| Scald | *Rynchosporium secalis* |
| Rusts | *Puccinia* spp. |
| Leaf spot | *Septoria tritici* |

Late Season Diseases:

| | |
|---|---|
| Rusts | *Puccinia* spp. |
| Glume blotch | *Septoria nodorum* |

EXAMPLE 2

The following mixture was prepared by dissolving the "SYNPERONIC" NPE 1800 into the imazalil which was itself mixed with the "SOLVESSO" 150 by warming to 50° C. and this solution was emulsified into water using a high shear stirrer. The flutriafol was bead milled with the "MORWET" 4425 to form a millbase. This millbase, together with the "KELZAN" M and the Polymeric Surfactant H190/396, was then stirred into the emulsion.

| | g/l |
|---|---|
| Flutriafol | 317 |
| Imazalil | 94 |
| "SOLVESSO" 150 | 8 |
| "MORWET" D425 | 16 |

-continued

|  | g/l |
|---|---|
| "SYNPERONIC" NPE 1800 | 17 |
| Polymeric Surfactant H190/396 | 56 |
| "KELZAN" M | 2 |
| Water to 1 liter | |

EXAMPLE 3

The following mixture was prepared using the procedure described in Example 2. The diclobutrazol was bead milled with the "MORWET" D425 to form a millbase.

|  | g/l |
|---|---|
| Diclobutrazol | 281 |
| Imazalil | 94 |
| "SOLVESSO" 150 | 8 |
| "MORWET" D425 | 14 |
| "SYNPERONIC" NPE 1800 | 17 |
| Polymeric Surfactant H190/396 | 56 |
| "KELZAN" M | 2 |
| Water to 1 liter | |

EXAMPLE 4

The following mixture was prepared using the procedure described in Example 1, the carbendazim being used to form a millbase with "POLFON" H as the surfactant and the prochloraz being incorporated into an emulsion. The millbase was stirred into the emulsion.

|  | g/l |
|---|---|
| Carbendazim | 40 |
| Prochloraz | 300 |
| Xylene | 175 |
| "POLYFON" H | 2 |
| "SPAN" 80 | 50 |
| "TWEEN" 40 | 50 |
| Urea | 120 |
| Polymeric Surfactant H190/396 | 10 |
| "KELZAN" M | 1 |
| Water to 1 liter | |

EXAMPLE 5

The following mixture was prepared using the procedure described in Examples 2 and 3. The propyzamide was formulated as a suspension (millbase) and the fluazifop-P-butyl as an emulsion. The millbase was incorporated into the emulsion by stirring.

|  | g/l |
|---|---|
| Propyzamide | 280 |
| Fluazifop-P-butyl | 28 |
| Kerosene | 22 |
| "MORWET" D425 | 47 |
| "SPAN" 80 | 0.25 |
| "TWEEN" 40 | 5.97 |
| Polymeric Surfactant H190/396 | 10 |
| "BENTOPHARM" | 10 |
| "KELZAN" M | 2 |
| Water to 1 liter | |

EXAMPLE 6

The following formulation was prepared initially on a laboratory scale of several liters and then scaled up to 150 liters.

|  | Concentration g/l |
|---|---|
| Diclobutrazol | 40 |
| Prochloraz | 300 |
| "SPAN" 80 | 50 |
| "TWEEN" 40 | 50 |
| Xylene | 114 |
| Urea | 120 |
| "KELZAN" M | 1 |
| Polymeric Surfactant H190/396 | 10 |
| "MORWET" D425 | 2.6 |
| "PROXEL" AB | 0.1 |
| Water to 1 liter | |

The diclobutrazol was bead milled at 500 g/l with the "MORWET" D425 (40 g/l) to form a millbase. The prochloraz was dissolved in the xylene along with the "SPAN" 80 and the "TWEEN" 40 by warming to 50° C. and the solution was then emulsified into a solution of the water, urea, "KELZAN" M (preswollen in water and containing "PROXEL" AB as a bactericide) and the Polymeric Surfactant H190/396. The whole was mixed using a high shear stirrer and mixing was continued for 3-5 minutes after the addition of the emulsion phase. The millbase was then stirred in as the final stage.

This formulation initially showed no flocculation of the diclobutrazol particles and a very fine prochloraz emulsion (droplet volume mean diameter 1 μm). At constant temperature storage some recrystallisation of diclobutrazol did occur but the largest crystals produced were 10 μm. Some of these crystals existed in small flocs but these were small in number and were not retained by a 150 μm mesh.

Prochloraz is a low melting point solid (mpt. 38.5°-41.0° C.) having the chemical formula:

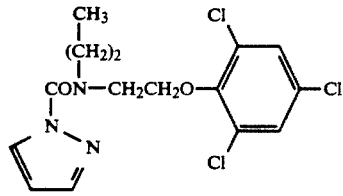

and the following chemical name (IUPAC): N-propyl-N-[2-(2,4,6-trichlorophenoxy)ethyl]-imidazole-1-carboxamide.

It can be formulated as an oil-in-water emulsion using a solution of it in xylene (or a "SOLVESSO" or other convenient solvent).

Diclobutrazol is a crystalline solid (mpt. 147°-149° C.) which can be formulated as a suspension concentrate. It has the formula:

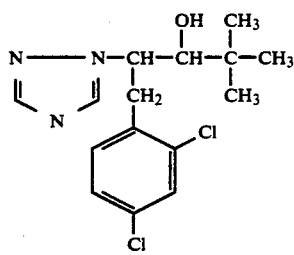

and the following chemical name (IUPAC): (2RS,3RS)-1-(2,4-dichlorophenyl)-4,4-dimethyl-2-(1H-1,2,4-triazol-1-yl)pentan-3-ol.

EXAMPLE 7

A large scale sample of the formulation of Example 6 was prepared but using 175 g/l xylene instead of 114 g/l. The same process as in Example 1 was deployed. This formulation showed similar stability properties as the Example 1 formulation but subsequent crystallisation of the prochloraz was lessened.

EXAMPLE 8

A formulation was prepared as in Example 7 except that the oil phase was kept at 50° C. for 24 hours before emulsification. This resulted in subsequent crystallisation of the prochloraz being substantially prevented.

EXAMPLE 9

The formulation was prepared as in Example 8 but with the addition of 1 g/l of the dye Fast Green FCF. This formulation showed no crystallisation of the prochloraz at 5° C., 0° C. or −5° C. after 3 months storage. Fast Green FCF is a product of B.D.H. (British Drug Houses) Limited and it is the sodium salt of the trisulphonated, oxidised condensate of p-hydroxybenzaldehyde with N-phenylbenzylamine (2 mol).

EXAMPLE 10

A formulation was prepared using the same process as in Example 7 but with a lower active ingredient content. The formulation contained the following:

|  | Concentration g/l |
| --- | --- |
| Prochloraz | 225 |
| Diclobutrazol | 30 |
| "SPAN" 80 | 50 |
| "TWEEN" 40 | 50 |
| Xylene | 226 |
| Urea | 120 |
| "KELZAN" M | 1 |
| Polymeric Surfactant H190/396 | 10 |
| "MORWET" D425 | 2.4 |
| "PROXEL" AB | 0.1 |
| Water to 1 liter |  |

This formulation also contained 1 g/l Fast Green FCF dye and crystallisation of the prochloraz was substantially prevented on storage.

EXAMPLE 11

The following mixture was prepared using the following procedure.

The chlorothalonil was bead milled at 800 g/l with the Polymeric Surfactant H190/396 (40 g/l). The hexaconazole was also bead milled at 500 g/l with the Polymeric Surfactant H190/396 (30 g/l). The "SYNPERONIC" NPE 1800 was dissolved into the tridemorph on warming to 50° C. This oil phase was then emulsified into a mixture of the water, urea, "KELZAN" M (preswollen with water to form a gel and containing the "PORXEL" AB as a bactericide) and the two millbases using a high shear stirrer. Mixing was continued for several minutes.

|  | g/l |
| --- | --- |
| Chlorothalonil | 375 |
| Hexaconazole | 62.5 |
| Tridemorph | 175 |
| Polymeric Surfactant H190/396 | 23 |
| "SYNPERONIC" NPE 1800 | 50 |
| Urea | 77 |
| "KELZAN" M | 0.5 |
| Water to 1 liter |  |

EXAMPLE 12

The following mixture was prepared by bead milling the chlorothanonil at 800 g/l with the "MORWET" D425 (50 g/l) to form a millbase. The hexaconazole was bead milled at 500 g/l with the "MORWET" D425 (25 g/l) to form a millbase. The "SYNPERONIC" NPE 1800 was dissolved into the tridemorph on warming to 50° C. The oil phase thus formed was then emulsified into a mixture of the water, propylene glycol, "KELZAN" M (as a pre-swollen gel containing "PROXEL" AB as a bactericide) and the chlorothalonil millbase using a high shear stirrer. After mixing for several minutes the hexaconazole millbase was stirred in as the final stage.

|  | g/l |
| --- | --- |
| Chlorothalonil | 375 |
| Hexaconazole | 62.5 |
| Tridemorph | 175 |
| "MORWET" D425 | 27 |
| "SYNPERONIC" NPE 1800 | 50 |
| Polymeric Surfactant H190/396 | 10 |
| Propylene glycol | 70 |
| "KELZAN" M | 0.5 |
| Water to 1 liter |  |

EXAMPLE 13

The following mixture was prepared using the procedure described in Example 11, the fenpropidin being formulated as an emulsion.

|  | g/l |
| --- | --- |
| Chlorothalonil | 300 |
| Hexaconazole | 50 |
| Fenpropidin | 225 |
| Polymeric Surfactant H190/396 | 18 |
| "SYNPERONIC" NPE 1800 | 50 |
| Urea | 87 |
| "KELZAN" M | 0.5 |
| Water to 1 liter |  |

EXAMPLE 14

The following mixture was prepared using the procedure described in Example 12, the fenpropidin being formulated as an emulsion.

|  | g/l |
| --- | --- |
| Chlorothalonil | 300 |
| Hexaconazole | 50 |
| Fenpropidin | 225 |
| "MORWET" D425 | 21 |
| "SYNPERONIC" NPE 1800 | 50 |
| Polymeric Surfactant H190/396 | 10 |
| Urea | 87 |
| "KELZAN" M | 0.5 |
| Water to 1 liter | |

We claim:

1. A pesticidal formulation comprising a mixture of an active ingredient formulated as an emulsion and one or more active ingredients each formed as a suspension wherein there is present a dispersing agent which is, or comprises, a block or graft copolymer the molecule of which comprises at least one component (A), of molecular weight at least 250, which is solvatable by the aqueous medium and at least one other component (B), of molecular weight at least 500 and having a minimum degree of hydrophobicity such that component B of the block or graft copolymer would, if it were unattached to the remainder of the copolymer molecule, be sufficiently hydrophobic to be insoluble both in water and in methanol, the total weight ratio of components A to individual components B in the copolymer molecule being from 10:1 to 1:2.

2. A formulation as claimed in claim 1 wherein the dispersing agent is a polymeric surfactant comprising an acrylic graft copolymer containing 36.6% methyl methacrylate, 1.9% methacrylic acid, both grafted with methoxy poly (ethylene glycol) 750 methacrylate (61.5%).

3. A formulation as claimed in claim 1 wherein an active ingredient formed as a suspension and which is a fungicidal substance which is a triazole or imidazole or a benzimidazole is in admixture with another active ingredient formed as an emulsion which is also a fungicidal substance and an imidazole or a morpholine or a triazole.

4. A formulation as claimed in claim 1 wherein a first active ingredient formed as a suspension is the herbicide propyzamide and a second active ingredient formed as an emulsion is the herbicide fluazifop-P-butyl.

5. A formulation as claimed in claim 1 which is a ternary mixture containing the active ingredients chlorothalonil and hexaconazole each formed as a suspension and either tridemorph or fenpropidin formed as an emulsion.

6. A formulation as claimed in claim 1 and containing one or more of the following: solvents, surface active agents, polysaccharides, bactericides, dyes, clays, lignosulphonates, urea, polyvinyl alcohol/acetate copolymer, water.

7. A formulation as claimed in claim 1 wherein the dispersing agent is an amphipathic polymeric stabiliser capable of associating with and entropically stabilising a non-ionic dispersion of particulate solids in an aqueous liquid and comprising a polymeric backbone provided by a random co-polymer, of alpha,beta-ethylenically unsaturated monomers with a molecular weight of at least 10,000, optionally containing ionizable groups, which is insoluble in the aqueous liquid, the polymeric backbone carrying at least two pendant chain-like non-ionic components of molecular weight at least 350 solvated by the aqueous liquid and distributed along the said backbone at intervals of less than 30 covalent links, the weight proportion of components solvated by the aqueous liquid being from 20 to 80 of the stabiliser molecule.

8. A process for preparing a mixture of pesticides which comprises milling one or more of the pesticides with water and a surfactant to form one or more millbases, dissolving a further pesticide, in a solvent if necessary, dissolving a surfactant in this oil phase, if necessary with warming, and then, using a high shear mixer for several minutes emulsifying the solution together with water, urea and also a high molecular weight linear polysaccharide formed as a gel by pre-swelling with water and optionally containing a bactericide, and a dispersing agent as defined, claim 1 thereafter stirring the millbase, or millbases into the emulsion so formed as a final stage.

9. A process as claimed in claim 8 where the surfactant used in the solution of the further pesticide is either (a) a condensate of nonyl phenol with alkylene oxides or (b) sorbitan mono-oleate together with a condensate of sorbitan mono-palmitate with ethylene oxide.

10. A process as claimed in claim 8 wherein the dispersing agent is an acrylic graft copolymer comprising methyl methacrylate and methacrylic acid grafted with methoxy poly(ethylene glycol) 750 methacrylate and, together with the high molecular weight linear polysaccharide, is added to the emulsion along with the millbase or millbases in the final stage.

11. A process as claimed in claim 8 wherein the dispersing agent is an acrylic graft copolymer comprising methyl methacrylate and methacrylic acid grafted with methoxy poly(ethylene glycol) 750 methacrylate and is incorporated into the millbase.

12. A formulation according to claim 1 wherein the active ingredient in the form of a suspension is a triazole and the active ingredient in the form of an emulsion is an imidazole.

13. A formulation according to claim 13 wherein the triazole in suspension is flutriafol and the imidazole in emulsion is prochloraz.

14. A formulation as claimed in claim 3 wherein the fungicidal substance is flutriafol, diclobutrazol, or carbenazim, and the other active fungicidal substance is imazalil, prochloraz, fenpropidin or propiconazole.

* * * * *